(12) United States Patent
Chowhan et al.

(10) Patent No.: US 8,313,754 B2
(45) Date of Patent: *Nov. 20, 2012

(54) OPHTHALMIC COMPOSITIONS CONTAINING A SYNERGISTIC COMBINATION OF TWO POLYMERS

(75) Inventors: Masood A. Chowhan, Arlington, TX (US); Huagang Chen, Arlington, TX (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/083,823

(22) Filed: Apr. 11, 2011

(65) Prior Publication Data

US 2011/0190203 A1 Aug. 4, 2011

Related U.S. Application Data

(63) Continuation of application No. 11/673,070, filed on Feb. 9, 2007, now Pat. No. 7,947,295, which is a continuation-in-part of application No. 10/863,169, filed on Jun. 8, 2004, now Pat. No. 7,709,012.

(60) Provisional application No. 60/478,253, filed on Jun. 13, 2003.

(51) Int. Cl.
*A61K 31/716* (2006.01)
*A61K 31/728* (2006.01)

(52) U.S. Cl. .......... 424/400; 424/427; 424/682; 514/54; 514/55; 514/57; 514/781

(58) Field of Classification Search .................. 424/422, 424/427, 682, 717, 78, 80; 514/781, 887, 514/912, 914
See application file for complete search history.

(56) References Cited

U.S. PATENT DOCUMENTS

| | | | |
|---|---|---|---|
| 3,355,336 A | 11/1967 | Lyerly | |
| 3,947,573 A * | 3/1976 | Rankin | 514/397 |
| 4,039,662 A | 8/1977 | Hecht et al. | |
| 4,120,949 A * | 10/1978 | Bapatla et al. | 424/78.04 |
| 4,136,173 A | 1/1979 | Pramoda et al. | |
| 4,343,787 A | 8/1982 | Katz | |
| 4,767,463 A | 8/1988 | Brode et al. | |
| 4,783,488 A | 11/1988 | Ogunbiyi et al. | |
| 5,075,104 A | 12/1991 | Gressel et al. | |
| 5,188,826 A | 2/1993 | Chandrasekaran et al. | |
| 5,204,325 A | 4/1993 | Lindstrom et al. | |
| 5,366,985 A | 11/1994 | Nakayama et al. | |
| 5,368,843 A | 11/1994 | Rennie | |
| 5,409,904 A | 4/1995 | Hecht et al. | |
| 5,460,834 A * | 10/1995 | Bhagat | 424/682 |
| 5,558,876 A * | 9/1996 | Desai et al. | 424/427 |
| 5,652,272 A | 7/1997 | Ogawa et al. | |
| 5,710,182 A | 1/1998 | Reunamki et al. | |
| 5,939,485 A | 8/1999 | Bromberg et al. | |
| 6,174,859 B1 | 1/2001 | Lezdey et al. | |
| 6,316,506 B2 | 11/2001 | Asgharian | |
| 6,379,692 B1 | 4/2002 | Rao | |
| 6,403,609 B1 | 6/2002 | Asgharian | |
| 6,486,138 B1 | 11/2002 | Asgharian et al. | |
| 6,583,124 B2 | 6/2003 | Asgharian | |
| 7,001,615 B1 | 2/2006 | Singh et al. | |
| 7,244,440 B2 | 7/2007 | Chowhan et al. | |
| 2003/0109424 A1 | 6/2003 | Shah et al. | |
| 2003/0232089 A1 | 12/2003 | Singh et al. | |
| 2004/0009893 A1 | 1/2004 | Wang et al. | |
| 2004/0118414 A1 | 6/2004 | Shah | |
| 2004/0241151 A1 | 12/2004 | Husmark et al. | |
| 2004/0253280 A1 | 12/2004 | Chowhan et al. | |
| 2005/0013854 A1 | 1/2005 | Mannino et al. | |
| 2006/0003964 A1 | 1/2006 | Shah et al. | |
| 2007/0128156 A1 | 6/2007 | Chowhan et al. | |
| 2007/0224159 A1 | 9/2007 | Chowhan et al. | |
| 2008/0193407 A1 | 8/2008 | Chowhan et al. | |

FOREIGN PATENT DOCUMENTS

| | | |
|---|---|---|
| CN | 1085106 | 4/1994 |
| DE | 34 40 352 | 5/1986 |
| EP | 0 531 529 | 11/1996 |
| EP | 0 663 208 | 5/1997 |
| JP | 7-196474 | 8/1995 |
| JP | 2002-255829 | 9/2002 |
| WO | 91/19481 | 12/1991 |
| WO | 92/00707 | 1/1992 |
| WO | WO-93/17664 | * 9/1993 |
| WO | 98/43643 | 10/1998 |
| WO | 99/06023 | 2/1999 |
| WO | 00/19981 | 4/2000 |
| WO | 02/49614 | 6/2002 |
| WO | 02/49615 | 6/2002 |
| WO | 02/060495 | 8/2002 |
| WO | 03/059391 | 7/2003 |
| WO | 2004/062660 | 7/2004 |

OTHER PUBLICATIONS

Arbuckle et al., "Stabilizers and Emulsifiers," Ice Cream, Avi Publishing Co., 1986, Chapter 6, pp. 84-94.
Australian Examiner's Report No. 2 for corresponding AU 2004249137 with Oct. 12, 2009 mailing date.
Carbopol® Product Brochure, B.F. Goodrich (1994).
Charoo et al., Preparation of in Situ-Forming Ophthalmic Gels of Ciprofloxacin Hydrochloride for the Treatment of Bacterial Conjunctivitis in Vitro and in Vivo Studies, .J. of Pharmaceutical Sciences, vol. 92(2), pp. 407-413 (2003).
EP 09168920.8 Extended European Search Report with Nov. 27, 2009 mailing date.
EP 09168920.8 Partial European Search Report with Sep. 28, 2009 mailing date.

(Continued)

*Primary Examiner* — Michael G Hartley
*Assistant Examiner* — Jagadishwar Samala
(74) *Attorney, Agent, or Firm* — Scott A. Chapple

(57) ABSTRACT

Ophthalmic compositions suitable for use as artificial tears or as vehicles for ophthalmic drugs are disclosed. The compositions contain a combination of two polymers that have a synergistic effect on viscosity.

18 Claims, No Drawings

OTHER PUBLICATIONS

Goldstein et al., "Guar Gum," Industrial Gums Polysaccharides and Their Derivatives, 2nd Edition, Academic Press, Chapter XIV, pp. 303-321 (1973).

Heyne et al., "Chemical Composition and Properties of Guar Polysaccharides," J. American Chemical Society, vol. 70, pp. 2249-2252 (1948).

Hoyt et al., "Friction Reduction as an Estimator of Molecular Weight," Polymer Letters, vol. 4, pp. 713-716 (1966).

JP 5-186348 Abstract, Jul. 27, 1993.

JP 11-228386 Abstract, Aug. 24, 1999.

PCT/US2004/018068 International Search Report and Written Opinion with Apr. 18, 2005 mailing date.

Rocks et al., "Xanthan Gum," Food Technology, vol. 25, pp. 22-29, (1971).

* cited by examiner

OPHTHALMIC COMPOSITIONS CONTAINING A SYNERGISTIC COMBINATION OF TWO POLYMERS

This application is a continuation of U.S. Ser. No. 11/673,070, filed Feb. 9, 2007 which is a continuation-in-part of U.S. Ser. No. 10/863,169, filed Jun. 8, 2004, which claims priority to U.S. Provisional Application, U.S. Ser. No. 60/478,253, filed Jun. 13, 2003, the disclosure of which is specifically incorporated by reference herein.

BACKGROUND OF THE INVENTION

1. Field of the Invention

The present invention relates to pharmaceutical compositions. In particular, this invention relates to topically administrable ophthalmic compositions that contain certain combinations of two polymeric components.

2. Description of Related Art

The use of polymeric ingredients in topically administrable ophthalmic compositions is well known. Polymeric ingredients are typically used in suspension compositions as physical stability aids, helping to keep the insoluble ingredients suspended or easily redispersible. In solution compositions, polymeric ingredients are typically used to increase the composition's viscosity.

Many polymers have been used in topically administrable ophthalmic compositions. Included among these are cellulosic polymers, such as hydroxypropyl methylcellulose, hydroxyethyl cellulose, and ethylhydroxyethyl cellulose. Also included are synthetic polymers, such as carboxyvinyl polymers and polyvinyl alcohol. Still others include polysaccharides such as xanthan gum, guar gum, and dextran.

Combinations of polymers have also been used in ophthalmic compositions. Certain combinations of polymers are known to provide synergistic effects on viscosity and, in some cases, even a phase transition from a liquid to a gel. For example, U.S. Pat. No. 4,136,173 discloses ophthalmic compositions containing a combination of xanthan gum and locust bean gum.

One approach to achieving a target viscosity in a topically administrable ophthalmic composition might involve simply adding a sufficient amount of one polymeric ingredient. Often, however, it is desirable to minimize the total amount of polymeric additives in topically administrable ophthalmic compositions. A mixed polymer system containing more than one polymer can significantly enhance the viscosity and lubrication property of a composition while minimizing total polymer concentration and cost of materials.

SUMMARY OF THE INVENTION

The present invention is directed toward aqueous ophthalmic compositions suitable for topical ophthalmic administration that comprise a viscosity enhancing amount of a polymeric ingredient wherein the polymeric ingredient consists of a certain combination of two polymeric ingredients. The ophthalmic compositions comprise a combination of polymeric ingredients selected from the group consisting of: hydroxypropyl methylcellulose and guar gum; hydroxypropyl methylcellulose and a carboxyvinyl polymer; carboxyvinyl polymer and guar gum; hydroxypropyl methylcellulose and hydroxyethylcellulose; hyaluronic acid and hydroxypropyl methylcellulose; hyaluronic acid and a carboxyvinyl polymer; and hyaluronic acid and guar gum. The compositions containing one of these select combinations of polymeric ingredients are useful as artificial tear products, and can also serve as vehicles for delivering ophthalmic drugs.

The present invention is based upon the finding that these select combinations of two polymers have a synergistic effect on viscosity.

DETAILED DESCRIPTION OF THE INVENTION

Unless otherwise indicated, all ingredient concentrations are listed as a weight/volume percentage basis (% w/v).

The ophthalmic compositions of the present invention are aqueous compositions that include a select combination of two polymeric ingredients. The combination is one of the following: hydroxypropyl methylcellulose and guar gum; hydroxypropyl methylcellulose and a carboxyvinyl polymer; a carboxyvinyl polymer and guar gum; hydroxypropyl methylcellulose and hydroxyethylcellulose; hyaluronic acid and hydroxypropyl methylcellulose; hyaluronic acid and a carboxyvinyl polymer; and hyaluronic acid and guar gum. All five types of individual polymers are known and have been used in ophthalmic compositions. All five types of polymers are also commercially available.

HPMC is commercially available from the Dow Chemical Company under the brand name Methocel®. HPMC is available in a variety of grades. Most preferred for use in the compositions of the present invention is Methocel E4M, (HPMC 2910), which has a number average molecular weight of approximately 86,000 dalton. The concentration of HPMC in the compositions of the present invention will generally range from 0.05-0.5%, and will preferably be 0.3%.

The guar gum ingredient can be guar gum or a guar gum derivative, such as the hydroxypropyl or hydroxypropyltrimonium chloride derivatives of guar gum. Guar and its derivatives are described in U.S. Pat. No. 6,316,506, the entire contents of which are hereby incorporated by reference. For purposes of the present application, "guar gum" includes unsubstituted guar gum and its substituted derivatives. Guar gum and many of its derivatives are commercially available from Rhone-Poulenc (Cranbury, N.J.), Hercules, Inc. (Wilmington, Del.) and TIC Gum, Inc, (Belcamp, Md.). A preferred derivative for use in the compositions of the present invention is hydroxypropyl guar ("HP-Guar"). The concentration of guar in the compositions of the present invention will generally range from 0.01-0.2%, and will preferably be 0.1%.

Carboxyvinyl polymers suitable for use in the present invention are also known as "carbomers" or carboxypolymethylene. They are commercially available from sources such as Noveon, Inc. (Cleveland, Ohio), which distributes them under the trade name Carbopol®. Carbopol polymers are crosslinked, acrylic acid-based polymers. They are crosslinked with allyl sucrose or allylpentaerythritol. Carbopol copolymers are polymers of acrylic acid, modified by $C_{10-30}$ alkyl acrylates, and crosslinked with allylpentaerythritol. A preferred carboxyvinyl polymer for use in the compositions of the present invention is a polymer of acrylic acid crosslinked with allyl sucrose or allylpentaerythritol, which is commercially available as Carbopol® 974P. The concentration of carbomer in the compositions of the present invention will generally range from 0.01-0.2%, and will preferably be 0.1%.

HEC is commercially available from Hercules Inc. (Aqualon Division) in a variety of grades, including Natrasol 250 LR, Natrasol 250 MR and Natrasol 250 HR. A preferred HEC for use in the compositions of the present invention is the NE grade material, which is commercially available as Natrasol 250HR. The concentration of HEC in the compositions of the present invention will generally range from 0.05-0.5%, and will preferably range from 0.1-0.2%.

Hyaluronic acid is commercially available from a variety of sources, including Genzyme and Hyaluron Inc. Hyaluronic acid is available in many grades, with molecular weights ranging from 100,000 to greater than 3 million dalton. As used herein, hyaluronic acid also encompasses the sodium salt form of hyaluronic acid, known as sodium hyaluronate, which is also commercially available.

The aqueous compositions of the present invention contain one of the specified combinations of polymers in a total polymer concentration range of 0.05-3.0%, preferably 0.2-2.0%.

In addition to the required combination of two polymeric ingredients, the aqueous compositions of the present invention may contain other ingredients as excipients. For example, the compositions may include one or more pharmaceutically acceptable buffering agents, preservatives (including preservative adjuncts), tonicity-adjusting agents, surfactants, solubilizing agents, stabilizing agents, comfort-enhancing agents, emollients, pH-adjusting agents and/or lubricants. Preferably, the aqueous composition does not contain any polymeric ingredients, other than the synergistic combination of the two polymeric ingredients specified above, with the exception of polymeric preservatives for compositions that contain a preservative. If the compositions contain a carbomer as one of the two polymers, then the compositions of the present invention do not contain any ionic tonicity-adjusting agent, such as sodium chloride, or other ionic excipients, such as boric acid, as these ingredients have a significant, detrimental effect on the composition's viscosity.

The compositions of the invention have a pH in the range of 4-9, preferably 6-8, and most preferably 6.5-7.5. If the compositions contain a carbomer, it is critical that the compositions are formulated so that the target pH is not exceeded. Once a target pH has been exceeded in compositions containing a carbomer, adding an acid such as hydrochloric acid to adjust the pH downward can compromise the synergistic viscosity. It is known that relatively small amounts of acid or salts, on the order of 0.005%, can have a significant effect on the viscosity of compositions containing a carbomer.

The compositions of the present invention generally have an osmolality in the range of 220-340 mOsm/kg, and preferably have an osmolality in the range of 235-300 mOsm/kg.

The aqueous compositions of the present invention are suitable for use as artificial tear products to relieve symptoms of dry eye. Alternatively, the compositions of the present invention may act as a vehicle for an ophthalmic drug. The compositions of the present invention may also be used as irrigating solutions for ophthalmic or other surgical procedures. Ophthalmic drugs suitable for use in the compositions of the present invention include, but are not limited to: anti-glaucoma agents, such as beta-blockers including timolol, betaxolol, levobetaxolol, carteolol, miotics including pilocarpine, carbonic anhydrase inhibitors, prostaglandins, seretonergics, muscarinics, dopaminergic agonists, adrenergic agonists including apraclonidine and brimonidine; anti-angiogenesis agents; anti-infective agents including quinolones such as ciprofloxacin, and aminoglycosides such as tobramycin and gentamicin; non-steroidal and steroidal anti-inflammatory agents, such as suprofen, diclofenac, ketorolac, rimexolone and tetrahydrocortisol; growth factors, such as EGF; immunosuppressant agents; and anti-allergic agents including olopatadine. The ophthalmic drug may be present in the form of a pharmaceutically acceptable salt, such as timolol maleate, brimonidine tartrate or sodium diclofenac.

Compositions of the present invention may also include combinations of ophthalmic drugs, such as combinations of (i) a beta-blocker selected from the group consisting of betaxolol and timolol, and (ii) a prostaglandin selected from the group consisting of latanoprost; 15-keto latanoprost; travoprost; and unoprostone isopropyl.

Although the amount of drug included in the compositions of the present invention will be whatever amount is therapeutically effective and will depend upon a number of factors, including the identity and potency of the chosen drug, the total concentration of drug will generally be about 5% or less.

The compositions of the present invention are preferably not formulated as solutions that gel upon administration to the eye. The compositions illustrated in the Examples below do not gel upon administration to the eye.

The compositions of the present invention may be topically applied to the eye or injected into the eye, depending upon the target site and disease or condition to be treated. To treat diseases or conditions inside the eye rather than at the surface of the eye, the compositions of the present invention may, for example, be administered by intravitreal injection, subconjunctival injection, sub-tenon injection, retrobulbar injection, suprachoroidal injection, or periocular injection. A syringe apparatus including an appropriately sized needle, for example, a 27 gauge needle or a 30 gauge needle, can be effectively used to inject the composition into the posterior segment of an eye of a human or animal. The combination of polymers may be particularly advantageous for injections into the eye for the following reasons: prevention of reflux, prolonged duration of action so as to increase the period of time between repeat injections, and reduction in the total amount of polymer required to achieve a target viscosity, thereby reducing the polymer disposition from back of the eye.

The following examples are presented to illustrate further various aspects of the present invention, but are not intended to limit the scope of the invention in any respect.

EXAMPLES

Example 1

Artificial Tear Composition

A representative formulation for an artificial tear product according to the present invention is shown in Table 1.

TABLE 1

| Ingredients | Concentration (% w/v) |
| --- | --- |
| Carbopol 974P | 0.1 |
| HP-Guar | 0.1 |
| Mannitol | 4.0 |
| NaOH/HCl | Qs to pH 7.0 |
| Purified water | Qs to 100 |

The composition shown in Table 1 can be prepared by at least two methods. One method involves adding the following ingredients slowly and in the following order to heated purified water (70-80° C.) (approximately 80% of the desired batch volume) with mixing: mannitol, Carbopol 974P, and HP-Guar (waiting until each ingredient is mixed well before adding the next). pH is then adjusted with 1N NaOH, and the remaining amount of purified water is added. The composition is then autoclaved at 121° C. for thirty minutes and subsequently cooled to room temperature with constant stirring.

An alternative method of preparing the composition shown in Table 1 is as follows. In a first container, add heated purified water (70-80%) (approximately 60% of the desired batch volume), then mix in mannitol, and then Carbopol 974P, waiting until each ingredient is mixed well before adding the next. Autoclave the resulting composition at 121° C. for thirty minutes, then allow the composition to cool to room temperature with constant stirring ("the Carbopol composition"). In a separate container, add purified water (approximately 30% of the desired batch volume), then mix in HP-Guar. Adjust the pH of the HP-Guar composition with 1N NaOH to pH 9. Autoclave the HP-Guar composition at 121° C. for thirty minutes, then allow it to cool to room temperature with constant stirring ("the HP-Guar composition"), then aseptically combine the HP-Guar composition with the Carbopol composition, and aseptically adjust the final pH to 7.0, if necessary, with 1N NaOH.

Example 2

Synergistic Effect on Viscosity (HPMC+Guar; HPMC+Carbomer; Carbomer+Guar

The compositions shown in Table 2 were prepared and their viscosity was determined using a Brookfield cone/plate viscometer with number 42 cone/plate set (30 rpm, at 25° C.) for less viscous samples (viscosity less than 20 cps) and number 52 cone/plate set (3 rpm, at 25° C.) for more viscous samples (viscosity more than 20 cps). Two people independently prepared the indicated samples and measured their viscosity values (n=1) for each person. The averages of each set of results are shown in Table 2.

TABLE 2

| | Composition (% w/v) | | | | | | |
|---|---|---|---|---|---|---|---|
| Ingredient | 1 | 2 | 3 | 4 | 5 | 6 | 7 |
| Mannitol | 4.0 | 4.0 | 4.0 | 4.0 | 4.0 | 4.0 | 4.0 |
| HPMC 2910 | — | 0.3 | — | — | 0.3 | 0.3 | — |
| Carbopol 974P | — | — | 0.1 | — | 0.1 | — | 0.1 |
| HP-Guar | — | — | — | 0.1 | — | 0.1 | 0.1 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 |
| Viscosity (cps) | 1.1 | 8.2 | 488.1 | 5.3 | 1339.5 | 32.3 | 1273.0 |
| Subst. Synergy@ | — | — | — | — | Yes | Yes | Yes |

@Subst. Synergy = substantial synergy: greater than 150% of the simple sum of the two respective single polymer solutions Example 3

Synergistic Effect on Viscosity (HPMC+HEC)

The compositions shown in Table 3 were prepared and their viscosity determined using a Brookfield cone/plate viscometer with number 42 cone/plate set (30 rpm, at 25° C.) for less viscous samples (viscosity less than 20 cps) and number 52 cone/plate set (3 rpm, at 25° C.) for more viscous samples (viscosity more than 20 cps). The HEC used in this experiment was Natrasol 250HR as shown in the following Table. Two people independently prepared the indicated samples and measured their viscosity values (n=1) for each person. The averages of each set of results are shown in Table 3.

TABLE 3

| | Composition (% w/v) | | | | | | | |
|---|---|---|---|---|---|---|---|---|
| Ingredient | 8 | 9 | 10 | 11 | 12 | 13 | 14 | 15 |
| Mannitol | 4.0 | 4.0 | 4.0 | 4.0 | 4.0 | 4.0 | 4.0 | 4.0 |
| HPMC 2910 | — | 0.3 | — | — | — | 0.3 | — | — |
| HP-Guar | — | — | 0.1 | — | — | — | 0.1 | — |
| Carbopol 974P | — | — | — | 0.1 | — | — | — | 0.1 |
| Natrasol 250HR | — | — | — | — | 0.1 | 0.1 | 0.1 | 0.1 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 | q.s. 100 |
| Viscosity (cps) | 1.0 | 8.0 | 5.2 | 465.9 | 3.0 | 27.7 | 10.9 | 642.0 |
| Subst. Synergy@ | — | — | — | — | — | Yes | No | No |

@Subst. Synergy = substantial synergy: greater than 150% of the simple sum of the two respective single polymer solutions Example 4

Lack of Synergistic Effect on Viscosity (Polyvinyl Alcohol+Chondroitin Sulfate; Polyvinyl Alcohol+Polyvinylpyrrolidone; Chondroitin Sulfate+Polyvinylpyrrolidone)

The compositions shown in Table 4 were prepared and their viscosity determined using a Brookfield cone/plate viscometer with number 42 cone/plate set (30 rpm, at 25° C.). Two people independently prepared the indicated samples and measured their viscosity values (n=1) for each person. The averages of each set of results are shown in Table 4. Airvol 523S is a commercially available polyvinyl alcohol polymer. Chondroitin sulfate is a commercially available polymer. PVP K90 is a commercially available polyvinyl pyrrolidone polymer.

TABLE 4

| | Composition (% w/v) | | | | | | |
|---|---|---|---|---|---|---|---|
| Ingredient | 16 | 17 | 18 | 19 | 20 | 21 | 22 |
| Mannitol | 4.0 | 4.0 | 4.0 | 4.0 | 4.0 | 4.0 | 4.0 |
| PVA (Airvol 523S) | — | 0.2 | — | — | 0.2 | 0.2 | — |
| Chondroitin Sulfate | — | — | 0.2 | — | 0.2 | — | 0.2 |
| PVP (K90) | — | — | — | 0.2 | — | 0.2 | 0.2 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 |
| Viscosity (cps) | 1.0 | 1.5 | 1.3 | 1.4 | 1.7 | 1.9 | 1.8 |
| Subst. Synergy@ | — | — | — | — | No | No | No |

* slight, transparent precipitate observed
@Subst. Synergy = substantial synergy: greater than 150% of the simple sum of the two respective single polymer solutions Example 5

Lack of Synergistic Effect on Viscosity (Polyvinyl Alcohol+Carbomer; Chondroitin Sulfate+Carbomer; Polyvinyl pyrrolidone Carbomer)

The compositions shown in Table 5 were prepared and their viscosity determined using a Brookfield cone/plate viscometer with number 42 cone/plate set (30 rpm, at 25° C.) for less viscous samples (viscosity less than 20 cps) and number 52 cone/plate set (3 rpm, at 25° C.) for more viscous samples (viscosity more than 20 cps). Two people independently prepared the indicated samples and measured their viscosity values (n=1) for each person. The averages of each set of results are shown in Table 5. Airvol 523S is a commercially available polyvinyl alcohol polymer. Chondroitin sulfate is a commercially available polymer. K90 is a commercially available polyvinylpyrrolidone polymer.

TABLE 5

| Ingredient | Composition (% w/v) | | | | | | |
|---|---|---|---|---|---|---|---|
| | 17 | 18 | 19 | 23 | 24 | 25 | 26 |
| Mannitol | 4.0 | 4.0 | 4.0 | 4.0 | 4.0 | 4.0 | 4.0 |
| PVA (Airvol 523S) | 0.2 | — | — | — | 0.2 | — | — |
| Chondroitin Sulfate | — | 0.2 | — | — | — | 0.2 | — |
| PVP (K90) | — | — | 0.2 | — | — | — | 0.2 |
| Carbopol 974P | — | — | — | 0.1 | 0.1 | 0.1 | 0.1 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 |
| Viscosity (cps) | 1.5 | 1.3 | 1.4 | 441.6 | 323.8 | 12.7 | N/A* |
| Subst. Synergy@ | — | — | — | — | No | No | No |

*PVP was incompatible with Carbopol 974P—it formed a precipitate.
@Subst. Synergy = substantial synergy: greater than 150% of the simple sum of the two respective single polymer solutions Example 6

Lack of Synergistic Effect on Viscosity (HPMC Dextran; Guar+Dextran; Carbomer+Dextran)

The compositions shown in Table 6 were prepared and their viscosity determined using a Brookfield cone/plate viscometer with number 42 cone/plate set (30 rpm, at 25° C.) for less viscous samples (viscosity less than 20 cps) and number 52 cone/plate set (3 rpm, at 25° C.) for more viscous samples (viscosity more than 20 cps). Two people independently prepared the indicated samples and measured their viscosity values (n=1) for each person. The averages of each set of results are shown in Table 6.

TABLE 6

| Ingredient | Composition (% w/v) | | | | | | | |
|---|---|---|---|---|---|---|---|---|
| | 27 | 28 | 29 | 30 | 31 | 32 | 33 | 34 |
| Mannitol | 4.0 | 4.0 | 4.0 | 4.0 | 4.0 | 4.0 | 4.0 | 4.0 |
| HPMC 2910 | — | 0.3 | — | — | — | 0.3 | — | — |
| HP-Guar | — | — | 0.1 | — | — | — | 0.1 | — |
| Carbopol 974P | — | — | — | 0.1 | — | — | — | 0.1 |
| Dextran 70 | — | — | — | — | 0.1 | 0.1 | 0.1 | 0.1 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 | q.s. 100 |
| Viscosity (cps) | 1.1 | 7.9 | 5.2 | 461.6 | 1.4 | 8.4 | 5.2 | 379.3 |
| Subst. Synergy@ | — | — | — | — | — | No | No | No |

@Subst. Synergy = substantial synergy: greater than 150% of the simple sum of the two respective single polymer solutions Example 7

Effect of Salt on Viscosity for a Polymer Combination that Contains Carbomer

The compositions shown below in Table 7 were prepared to determine the effect of the addition of salt (NaCl) on viscosity. The viscosity of each sample was determined using a Brookfield cone/plate viscometer (52 cone, 3 rpm). The results are shown in Table 7.

TABLE 7

| INGREDIENT | Composition (% w/v) | | | | |
|---|---|---|---|---|---|
| | 35 | 36 | 37 | 38 | 39 |
| Mannitol | 4.0 | 4.0 | 4.0 | 4.0 | 4.0 |
| HPMC 2910 | 0.3 | 0.3 | 0.3 | 0.3 | 0.3 |
| Carbopol 974P | 0.1 | 0.1 | 0.1 | 0.1 | 0.1 |
| NaCl | 0 | 0.001 | 0.005 | 0.01 | 0.05 |
| NaOH/HCl | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 |
| Viscosity (cps) | 737 | 430 | 359 | 212 | 49 |

Example 8

Effect of Boric Acid on Viscosity for a Polymer Combination that Contains Carbomer The compositions shown below in Table 8 were prepared to determine the effect of the addition of boric acid on viscosity. The viscosity of each sample was determined using a Brookfield cone/plate viscometer (52 cone, 3 rpm). The results are shown in Table 8.

TABLE 8

| INGREDIENT | Composition (% w/v) | | | | |
|---|---|---|---|---|---|
| | 40 | 41 | 42 | 43 | 44 |
| Mannitol | 4.0 | 4.0 | 4.0 | 4.0 | 4.0 |
| HPMC 2910 | 0.3 | 0.3 | 0.3 | 0.3 | 0.3 |
| Carbopol 974P | 0.1 | 0.1 | 0.1 | 0.1 | 0.1 |
| Boric acid | 0 | 0.001 | 0.005 | 0.01 | 0.05 |
| NaOH/HCl | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 |
| Viscosity (cps) | 657 | 534 | 362 | 233 | 65 |

Example 9

Synergistic Effect on Viscosity (HA+HPMC; HA+Carbomer; HA+Guar)

The compositions shown in Table 9 were prepared. The viscosity of each composition was determined using a Brookfield cone/plate viscometer with number 42 cone/plate set (30 rpm, at 25° C.) for less viscous samples (viscosity less than 20 cps) and number 52 cone/plate set (6 rpm, at 25° C.) for more viscous samples (viscosity more than 20 cps). The results are shown in Table 9.

TABLE 9

| Ingredient | \multicolumn{7}{c}{Composition (% w/v)} | | | | | | |
|---|---|---|---|---|---|---|---|
| | 45 | 46 | 47 | 48 | 49 | 50 | 51 |
| Mannitol | 4.0 | 4.0 | 4.0 | 4.0 | 4.0 | 4.0 | 4.0 |
| Sodium Hyaluronate | 0.1 | — | — | — | 0.1 | 0.1 | 0.1 |
| HPMC 2910 | — | 0.3 | — | — | 0.3 | — | — |
| Carbopol 974P | — | — | 0.1 | — | — | 0.1 | — |
| HP-Guar | — | — | — | 0.1 | — | — | 0.1 |
| NaOH/HCl | q.s. pH 7.0 | q.s. pH 7.0 | q.s. pH 7.0 | q.s. pH 7.0 | q.s. pH 7.0 | q.s. pH 7.0 | q.s. pH 7.0 |
| Purified Water | q.s. 100 | q.s. 100 | q.s. 100 | q.s. 100 | q.s. 100 | q.s. 100 | q.s. 100 |
| Final pH | 6.93 | 7.06 | 6.96 | 6.99 | 7.08 | 7.06 | 6.94 |
| Viscosity (cps) | 125.9 | 8.0 | 432.3 | 5.6 | 267 | 873.5 | 232.3 |
| Subst. Synergy@ | — | — | — | — | Yes | Yes | Yes |

@Subst. Synergy = substantial synergy: greater than 150% of the simple sum of the two respective single polymer solutions

Example 10

Synergistic Effect on Viscosity (HA+Carbomer; HA+Guar; Carbomer+Guar)

The compositions shown in Table 10 were prepared. The viscosity of each composition was determined using a Brookfield cone/plate viscometer with number 42 cone/plate set (30 rpm, at 25° C.) for less viscous samples (viscosity less than 20 cps) and number 52 cone/plate set (6 rpm, at 25° C.) for more viscous samples (viscosity more than 20 cps). The results are shown in Table 10.

TABLE 10

| Sample Descriptions | 52 | 53 | 54 | 55 | 56 | 57 |
|---|---|---|---|---|---|---|
| | | | | \multicolumn{3}{c}{Two Component System} | | |
| Mannitol (%) | 4 | 4 | 4 | 4 | 4 | 4 |
| Sodium Hyaluronate | 0.1 | | | 0.1 | 0.1 | |
| Carbopol 974P (%) | | 0.1 | | 0.1 | | 0.1 |
| HP Guar | | | 0.1 | | 0.1 | 0.1 |
| pH | 7.0 | 7.0 | 7.0 | 7.0 | 7.0 | 7.0 |
| To Make: | | | | | | |
| Mannitol (g) | 4 | 4 | 4 | 4 | 4 | 4 |
| Sodium Hyaluronate (g) | 0.1 | | | 0.1 | 0.1 | 0 |
| Carbopol 974P (g) | | 0.1 | | 0.1 | 0 | 0.1 |
| HP Guar (g) | | | 0.1 | 0 | 0.1 | 0.1 |
| Total Volume (mL) | 100 | 100 | 100 | 100 | 100 | 100 |
| Physical Parameter | | | | | | |
| Final pH | 7.02 | 7.08 | 6.93 | 6.93 | 7.04 | 6.96 |
| Mean Viscosity (cps) (n = 2) | 125.5 | 466.5 | 4.55 | 930 | 257.5 | 1184 |
| Viscosity Synergy Analysis | | | | | | |
| % Viscosity Increased* | NA | NA | NA | 157% | 198% | 251% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. An aqueous composition suitable for topical ophthalmic administration comprising:
    an ophthalmically acceptable drug;
    a viscosity enhancing amount of a combination of two polymers having a synergistic effect on the composition's viscosity, the combination of two polymers being hydroxypropyl methylcellulose (HPMC) and hydroxyethylcellulose (HEC), wherein the concentration of HPMC is in a range from 0.05 to 0.5% and HEC is in a range from 0.05 to 0.5%;
    wherein the aqueous composition has a viscosity that is greater than 150% of a sum of viscosities of two solutions, each of the two solutions respectively including only one of the two polymers.

2. The composition of claim 1 wherein the total concentration of the two polymers ranges from 0.05-3.0% (w/w).

3. The composition of claim 1 wherein the total concentration of the two polymers ranges from 0.2-2.0% (w/w).

4. The composition of claim 3 wherein the concentration of HEC in the composition is in a range from 0.1 to 0.2%.

5. The composition of claim 3 wherein the concentration of HPMC in the composition is in a range from 0.05 to 0.5%.

6. The composition of claim 1 further comprising an ingredient selected from the group consisting of pharmaceutically acceptable buffering agents; preservatives; non-ionic tonicity-adjusting agents; surfactants; solubilizing agents; stabilizing agents; comfort-enhancing agents; emollients; pH-adjusting agents; and lubricants.

7. The composition of claim 1 wherein the ophthalmic drug is selected from the group consisting of anti-glaucoma agents; anti-angiogenesis agents; anti-infective agents; non-steroidal and steroidal anti-inflammatory agents; growth factors; immunosuppressant agents; and anti-allergic agents.

8. The composition of claim 1 wherein the concentration of HEC in the composition is in a range from 0.1 to 0.2%.

9. The composition of claim 1 wherein the ophthalmic drug is selected from the group consisting of anti-glaucoma agents; anti-angiogenesis agents; anti-infective agents; non-steroidal and steroidal anti-inflammatory agents; growth factors; immunosuppressant agents; and anti-allergic agents.

10. The composition of claim 1 wherein the ophthalmic drug is selected from anti-glaucoma agents; anti-angiogenesis agent and anti-allergic agents.

11. An aqueous composition suitable for topical ophthalmic administration comprising:
   an ophthalmically acceptable drug;
   a viscosity enhancing amount of a combination of two polymers having a synergistic effect on the composition's viscosity, the combination of two polymers being hydroxypropyl methylcellulose (HPMC) and hydroxyethylcellulose (HEC), wherein the concentration of HPMC is in a range from 0.05 to 0.5% and HEC is in a range from 0.05 to 0.5% wherein the aqueous composition is free of any polymers other than hydroxypropyl methylcellulose and hydroxyethyl cellulose;
   wherein the aqueous composition has a viscosity that is greater than 150% of a sum of viscosities of two solutions, each of the two solutions respectively including only one of the two polymers.

12. The composition of claim 11 wherein the total concentration of the two polymers ranges from 0.05-3.0% (w/w).

13. The composition of claim 11 wherein the total concentration of the two polymers ranges from 0.2-2.0% (w/w).

14. The composition of claim 13 wherein the concentration of HEC in the composition is in a range from 0.1 to 0.2%.

15. The composition of claim 14 wherein the concentration of HPMC in the composition is in a range from 0.05 to 0.5%.

16. The composition of claim 11 wherein the ophthalmic drug is selected from the group consisting of anti-glaucoma agents; anti-angiogenesis agents; anti-infective agents; non-steroidal and steroidal anti-inflammatory agents; growth factors; immunosuppressant agents; and anti-allergic agents.

17. The composition of claim 11 wherein the concentration of HEC in the composition is in a range from 0.1 to 0.2%.

18. The composition of claim 11 wherein the ophthalmic drug is selected from anti-glaucoma agents; anti-angiogenesis agent and anti-allergic agents.

* * * * *